United States Patent [19]
Baur et al.

[11] Patent Number: 5,683,553
[45] Date of Patent: Nov. 4, 1997

[54] PREPARATION OF 3-CHLOROPHTHALIC ANHYDRIDE

[75] Inventors: Karl Gerhard Baur, Ludwigshafen; Erwin Brunner, Weinheim; Eckhardt Brandt, Schifferstadt, all of Germany

[73] Assignee: BASF Aktiengesellschaft, Ludwigshafen, Germany

[21] Appl. No.: 580,252

[22] Filed: Dec. 28, 1995

[30] Foreign Application Priority Data

Jan. 2, 1995 [DE] Germany ............... 195 00 031.5

[51] Int. Cl.$^6$ ................................................. B01D 3/42
[52] U.S. Cl. ................... 203/1; 203/73; 203/74; 203/77; 203/80; 549/250
[58] Field of Search ............ 203/1, 80, DIG. 16, 203/73, 74, 77, DIG. 11; 549/250

[56] References Cited

U.S. PATENT DOCUMENTS

| 3,650,906 | 3/1972 | Gehrken et al. | 203/89 |
| 3,787,364 | 1/1974 | Wirth et al. | 528/170 |
| 3,886,050 | 5/1975 | Deutner et al. | 203/80 |
| 4,008,255 | 2/1977 | Wirth et al. | 203/70 |
| 4,430,163 | 2/1984 | Albers et al. | 203/75 |
| 4,514,572 | 4/1985 | Hamprecht et al. | 549/246 |

FOREIGN PATENT DOCUMENTS 638 200 10/1936 Germany .
628 401 8/1949 United Kingdom .

OTHER PUBLICATIONS

J. Chem. Soc., E.E. Ayling, 1929, pp. 253–265.

J. Am. Chem. Soc., Newman et al., vol. 78, 1956, pp. 5004–5007.

J. Org. Chem., vol. 43, No. 19, 1978, Zweig et al., pp. 3690–3692.

Primary Examiner—Virginia Manoharan
Attorney, Agent, or Firm—Keil & Weinkauf

[57] ABSTRACT

A process for preparing essentially pure 3-chlorophthalic anhydride from a mixture in which 3-chlorophthalic anhydride is present in addition to 4,5-dichlorophthalic anhydride, which involves first distilling off a mixture of 3-chlorophthalic anhydride and 4,5-dichlorophthalic anhydride, so that the obtained bottoms is essentially free of 4,5-dichlorophthalic anhydride, and then by distillation of the obtained bottoms, recovering 3-chlorophthalic anhydride in a second distillation step. The starting mixture is preferably prepared without solvent in a melt by incomplete chlorination of phthalic anhydride using FeCl$_3$ as a catalyst.

10 Claims, 1 Drawing Sheet

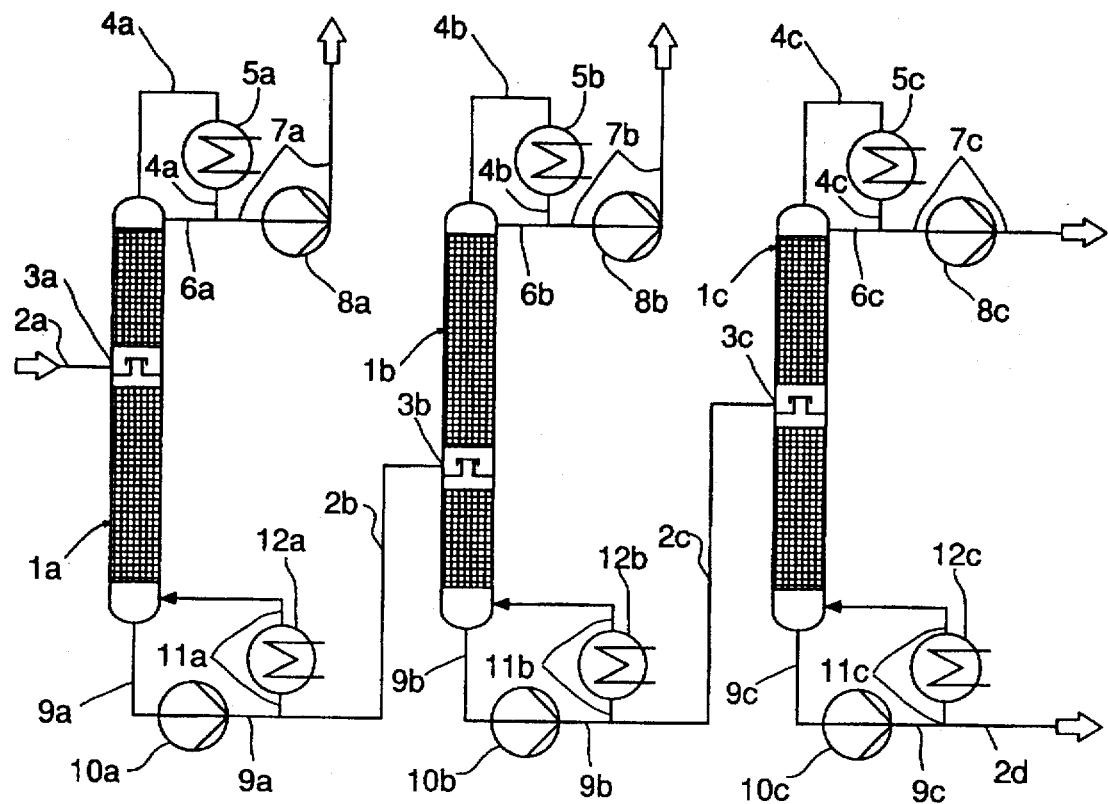

PREPARATION OF 3-CHLOROPHTHALIC ANHYDRIDE

SUMMARY OF THE INVENTION

The present invention relates to a process for preparing essentially pure 3-chlorophthalic anhydride from a mixture in which 3-chlorophthalic anhydride is present in addition to 4,5-dichlorophthalic anhydride.

BACKGROUND OF THE INVENTION

On account of their reactivity, monochlorinated phthalic anhydrides are sought-after intermediates, for example for preparing heterocycles, as dye precursors and recently also for preparing polymers. For these intended uses they are usually needed in high purity. While the preparation of 4-chlorophthalic anhydride in a simple manner in high yield by chlorination with sodium hypochlorite has been disclosed (GB Patent 628401, cf. also E. E. Ayling, J. Chem. Soc. (1929), 253), the preparation of pure 3-chlorophthalic anhydride is difficult.

Pure 3-chlorophthalic anhydride can be obtained by oxidation of 3-chloro-o-xylene, for example with nitric acid at elevated temperature and elevated pressure and subsequent conversion to the anhydride of the 3-chlorophthalic acid formed in the oxidation. The isomerically pure 3-chloro-o-xylene is obtained by distillative separation of the products of the nuclear chlorination of o-xylene, but this distillative separation is extremely complicated because of the low boiling point differences (relative volatilities) of 3- and 4-chloro-o-xylene. An industrial column for the simultaneous preparation of 3-chloro-o-xylene and 4-chloro-o-xylene in purities of, in each case, above 99% needs, in the case of continuous operation, approximately 250 theoretical separation stages. Other separation processes for separating the isomers, such as fractional crystallization, are no less complicated.

3-Chlorophthalic anhydride can also be prepared from 3-nitrophthalic anhydride by replacement of the nitro group by chlorine. The 3-nitrophthalic anhydride needed for this is prepared in three process steps by nitration of phthalic anhydride in moderate yield, by isomer separation of the nitrophthalic acids formed, by fractional crystallization and by conversion to the anhydride of the 3-nitrophthalic acid obtained (M. S. Newman, P. G. Scheurer, J. Am. Chem. Soc. 78 (1956), 5005; Organic Syntheses, Coll. Vol. 1 (1932), 399–401). This multistage and complicated route, which additionally gives poor yields, is not very suitable for industrial use.

The simplest synthesis of the monochlorinated phthalic anhydrides, namely the chlorination of phthalic anhydride using Lewis acid catalysts, leads, only with very low conversions, to mixtures which only contain the two isomeric 3- and 4-chlorophthalic anhydrides which are separable by distillation; as soon as the conversion rates reach economically acceptable values, more highly chlorinated phthalic anhydrides are always also formed (A. Zweig and M. Epstein, J. Org. Chem. 43 (1978), No. 19, pages 3690–3692). According to the present state of knowledge, recovery of essentially pure 3-chlorophthalic anhydride from this mixture under economically acceptable conditions, ie. by distillative separation or another process which can be carried out on a large scale, did not appear possible.

The difficulty in the distillative separation of the product mixture of a chlorination of phthalic anhydride using Lewis Acid catalysts lies in the separation of 3-chlorophthalic anhydride and 4,5-dichlorophthalic anhydride, which according to the literature has exactly the same boiling points, 313° C. at normal pressure. A. Zweig and M. Epstein, loc. cit., were only able to obtain mixtures of these two chlorination products.

Table I below gives a survey of the boiling points at normal pressure and melting points of the products obtained in the chlorination of phthalic anhydride which are given in the literature.

TABLE I

|  | B.p. (normal pressure) °C. | M.p. °C. |
|---|---|---|
| Phthalic anhydride | 284.5[1] | 131.6[2] |
| 4-Chlorophthalic anhydride | 294–295[2] | 98.5[2] |
| 3-Chlorophthalic anhydride | 313[3] | 124[2] |
| 4,5-Dichlorophthalic anhydride | 313[2] | 188[2] |
| 3,4-Dichlorophthalic anhydride | 329[2] | 121[2] |
| 3,6-Dichlorophthalic anhydride | 339[2] | 194.5[2] |
| 3,5-Dichlorophthalic anhydride | not formed in the chlorination of phthalic anhydride | |

[1]D'Ans Lax Taschenbuch für Chemiker und Physiker (D'Ans Lax handbook for chemists and physicists) 1983
[2]Handbook of Chemistry and Physics 1987–1988
[3]BASF measurement It emerges from the table that the boiling points of the dichlorinated reaction products other than 4,5-dichlorophthalic anhydride are distinctly higher, so their separation is possible without difficulties by distillation. The separation of phthalic anhydride and pure 4-chlorophthalic anhydride from the product mixture is also prior art; in particular 4-chlorophthalic anhydride, which is of economic interest, can be obtained in high purity by corresponding choice of the distillation parameters. On account of the high melting points of the products obtained, the boiling point ranges applicable with modification of the pressure are restricted.

A. Zweig and M. Epstein further report that the separation of 3-chlorophthalic anhydride and 4,5-dichlorophthalic anhydride cannot be successfully performed even by fractional recrystallization, fractional fusion, extraction and sublimation. These authors succeeded in carrying out the separation only by means of a polar gas-liquid chromatography column, which is unacceptable for preparation on an industrial scale.

As mentioned above, these authors also investigated the product ratio of the chlorination as a function of the reaction time, ie. the conversion of phthalic anhydride. Table II below, which is taken from A. Zweig and M. Epstein, loc. cit., illustrates that at higher conversions of phthalic anhydride in a chlorination with chlorine and iron(III) chloride in 1,1,2,2-tetrachloro-ethane, the proportion of the monochlorinated products decreases in favor of the proportion of the more highly chlorinated products, which is to be attributed to the approximately equal reactivity of the monochlorinated products and of phthalic anhydride itself.

TABLE II

| | Reaction time (h) | | | | |
|---|---|---|---|---|---|
| | 4 | 7 | 10 | 10.75 | 12.50 |
| Product mixture | | % by weight | | | |
| Phthalic anhydride (PA) | 83.2 | 25.0 | 4.7 | 1.6 | 0.6 |
| 4-Chloro PA | 9.8 | 32.3 | 31.7 | 27.0 | 19.5 |
| 3-Chloro PA | 7.0 | 24.9 | 19.0 | 17.6 | 14.0 |
| 4,5-Dichloro PA | | 2.5 | 6.0 | 7.0 | 8.2 |

TABLE II-continued

|  | Reaction time (h) | | | | |
| --- | --- | --- | --- | --- | --- |
|  | 4 | 7 | 10 | 10.75 | 12.50 |
| Product mixture | | | % by weight | | |
| 3,4-Dichloro PA |  | 7.7 | 18.4 | 21.9 | 25.1 |
| 3,6-Dichloro PA |  | 7.7 | 18.4 | 21.9 | 25.2 |
| 3,4,6-Trichloro PA |  |  |  | 3.0 | 7.3 |

The above findings previously allowed it to appear impossible to obtain 3-chlorophthalic anhydride in an economical manner from a direct chlorination reaction of phthalic anhydride.

It is an object of the present invention to provide a preparation process for 3-chlorophthalic anhydride which is not based on a multistage synthesis and otherwise is also economical.

We have found that this object is achieved by a process such as is defined in the claims. This is a process for preparing essentially pure 3-chlorophthalic anhydride from a mixture which contains 4,5-dichlorophthalic anhydride in addition to 3-chlorophthalic anhydride, which comprises, for the separation of 3-chlorophthalic anhydride and 4,5-dichlorophthalic anhydride, first distilling off a mixture of 3-chlorophthalic anhydride and 4,5-dichlorophthalic anhydride so that the bottom is essentially free of 4,5-dichlorophthalic anhydride, and then recovering 3-chlorophthalic anhydride by distillation.

Preferred embodiments are indicated in the subsidiary claims and the following description.

It has surprisingly been found that, against the trend pointed to by A. Zweig and M. Epstein, the distillative separation of 3-chlorophthalic anhydride and 4,5-dichlorophthalic anhydride is possible. To do this, small losses of 3-chlorophthalic anhydride which hardly affect the economy of the process must be accepted. These losses are all the lower, the lower the content of 4,5-dichlorophthalic anhydride in the chlorination mixture, which, as explained above, depends on the conversion of the phthalic anhydride in the chlorination.

Preferably, the process is carried out such that the mixture of 3-chlorophthalic anhydride and 4,5-dichlorophthalic anhydride is distilled off in the first distillation step at from 2.5 to 80 kPa, preferably 3 to 20 kPa, and from 185° to 300° C., preferably 190° to 250° C.

From the chlorination mixture of a chlorination of phthalic anhydride with Lewis acid catalysts, as known and as foreseeable on account of the vapor pressures, unreacted phthalic anhydride and 4-chlorophthalic anhydride can be distilled off in succession or together if neither the recycling of phthalic anhydride nor the recovery of 4-chlorophthalic anhydride is desired. These distillations can be carried out continuously or batchwise, and the purity of the components can be determined by the distillation requirement. After these distillation steps, a product mixture remains in the bottom which, at conversion rates of phthalic anhydride which are not too high, is composed mainly of 3-chlorophthalic anhydride and 4,5-dichlorophthalic anhydride and further of 3,4- and 3,6-dichlorophthalic anhydride and small amounts of trichlorinated products.

With an adequate number of separation steps and adequate reflux, the further distillation of this mixture surprisingly yields a top product in which the ratio of 4,5-dichlorophthalic anhydride to 3-chlorophthalic anhydride is distinctly increased compared with the ratio in the bottom. This fraction can be obtained until essentially no 4,5-dichlorophthalic anhydride is any longer present in the bottom of the column. Taking into consideration the identical boiling points and the identical trend of the vapor pressures, this behavior of the mixture was not foreseeable and is also in contrast to that described by A. Zweig and M. Epstein, loc. cit.

The 4,5-dichlorophthalic anhydride-free bottom product consists of 3-chlorophthalic anhydride, the other dichlorinated compounds and more highly chlorinated products. The preparation of 3-chlorophthalic anhydride in pure form takes place in a subsequent continuous or batchwise distillation step in which it is quantitatively separated from the next higher-boiling component, 3,4-dichlorophthalic anhydride. 3,6-Dichlorophthalic anhydride and trichlorinated compounds have still higher boiling points than 3,4-dichlorophthalic anhydride and are thus of no importance for the preparation of pure 3-chlorophthalic anhydride by distillation. After recovery of 3-chlorophthalic anhydride, the bottom product of the distillation process described can be converted into perchlorophthalic anhydride according to a further embodiment of the invention.

The size of the intermediate fraction of 4,5-dichlorophthalic anhydride and 3-chlorophthalic anhydride is predetermined by the content of 4,5-dichlorophthalic anhydride in the chlorination product mixture and can likewise be processed further to give the perchlorophthalic anhydride used as a dye precursor.

The invention thus permits the preparation of pure 3-chlorophthalic anhydride and, if desired, the simultaneous preparation of pure 4-chlorophthalic anhydride in good yield, in particular based on the sum of the two isomers, while the formation of more highly chlorinated by-products, which may be undesired, as a result of an incomplete conversion in the chlorination of phthalic anhydride, can be kept comparatively low.

In the course of the investigations on the product mixture from a chlorination reaction of phthalic anhydride, some of the boiling points of highly purified samples given in the literature were also checked. A comparison takes place in Table III below:

TABLE III

| Boiling points at normal pressure (°C.) | | |
| --- | --- | --- |
|  | Lit.[1] | BASF |
| 4-Chlorophthalic anhydride | 294–295[720] | 297.3 |
| 3-Chlorophthalic anhydride | 313 | 315.2 |
| 4,5-Dichlorophthalic anhydride | 313 | 314.5 |
| 3,6-Dichlorophthalic anhydride | 339 | 340.7 |

[1]see Table I

The preparation of 3-chlorophthalic anhydride according to the invention in high purity is economically far superior to the other processes described, such as preparation via the nitro compound or via the oxidation of 3-chloro-o-xylene.

BRIEF DESCRIPTION OF THE DRAWINGS

FIG. 1 is a schematic representation of an apparatus suitable for continuously carrying out the process according to the invention can be seen in the FIGURE.

DESCRIPTION OF THE PREFERRED EMBODIMENTS

In this FIGURE, 3 distillation columns for carrying out the process according to the invention are designated by 1a, 1b and 1c. In a known manner, these columns contain packing material or rectification plates, namely such that the column 1a contains 25 rectification steps, the column 1b 42 rectification steps and the column 1c 54 rectification steps. The feed lines 2a, 2b and 2c enter the columns 1a, 1b and 1c at the 15th, 8th or 25th rectification step. At the top of the columns 1a, 1b and 1c, the lines 4a, 4b and 4c lead to the condensers 5a, 5b and 5c and further to the lines 6a, 6b and 6c, which lead back to the column tops, and also to the lines 7a, 7b and 7c, which lead via the pumps 8a, 8b and 8c to distillation product containers (not shown). The lines 9a, 9b and 9c lead via the pumps 10a, 10b and 10c from the lower end of the columns 1a, 1b and 1c both to the lines 11a, 11b and 11c, which lead back via the evaporators 12a, 12b and 12c to the lower column ends of the columns 1a, 1b and 1c, and also to the feed lines 2b, 2c and 2d of the columns 1b and 1c and a further column (not shown).

The process according to the invention in this plant is carried out in an exemplary embodiment of the invention in a manner such that a solvent-free crude distillate of a chlorination reaction of phthalic anhydride is first fed into the column 1a via the feed line 2a. At the top of the column 1a, a part of the distillate which essentially contains phthalic anhydride is removed at 178.3° C. and 0.058 bar via the line 4a, the condenser 5a, and the line 7a with the aid of the pump 8a, while the greatest part of the distillate is fed back into the column 1a via the line 6a after condensation in the condenser 5a. The bottom from the column 1a is kept at 203.8° C. with the aid of the pump 10a, by passing it through the lines 9a and 11a and through the evaporator 12a; a part of the essentially phthalic anhydride-free bottom product of the column 1a is fed continuously to the column 1b at its 8th step via the line 2b. At the top of the column 2b, 4-chlorophthalic anhydride is distilled off at 176.3° C. and a pressure of 0.034 bar in a similar manner as in the column 1a, while the 4-chlorophthalic anhydride-free bottom is kept at 204.4° C. in a similar manner as in the column 1a and fed to the column 1c at its 25th step via the line 2c. At the top of the column 1c, a mixture of 3-chlorophthalic anhydride and 4,5-dichlorophthalic anhydride is removed at 186.6° C. and 0.03 bar. The bottom from the column 1c is kept at 205° C. and fed, as an essentially 4,5-dichlorophthalic anhydride-free product which contains the remaining 3-chlorophthalic anhydride, via the feed line 2d to a further column in which the remaining 3-chlorophthalic anhydride can be virtually quantitatively recovered continuously or batchwise in a customary manner.

The following examples illustrate the invention further. The chlorination reactions of phthalic anhydride were carried out in a melt without use of a solvent using $FeCl_3$ as a catalyst up to the conversion of phthalic anhydride given in the examples. In these reactions, remarkably, in each case somewhat more 3-chlorophthalic anhydride was formed than 4-chlorophthalic anhydride.

EXAMPLE 1

From a crude distillate of a chlorination reaction of phthalic anhydride, consisting of 57.00% by weight of phthalic anhydride, 18.30% by weight of 4-chlorophthalic anhydride, 20.50% by weight of 3-chlorophthalic anhydride, 0.90% by weight of 4,5-dichlorophthalic anhydride, 1.70% by weight of 3,6-dichlorophthalic anhydride and 1.60% by weight of higher-boiling products, 3-chlorophthalic anhydride having a residual content of 4,5-dichlorophthalic anhydride of 0.1% by weight is to be obtained. The crude distillate is fed into the column 1a at the height of the 15th step at a charge rate of 2000 kg/h. The distillate which is removed via the line 7a of the column 1a contains 99.50% by weight of phthalic anhydride and 0.50% by weight of 4-chlorophthalic anhydride at a reflux ratio of 24 [reflux/ material escaping at the top]. From the column 1b via the line 7b at a reflux ratio of 466, a distillate is removed which consists of 0.50% by weight of phthalic anhydride and 99.50% by weight of 4-chlorophthalic anhydride and also 10 ppm of 3-chlorophthalic anhydride. The bottom of the column 1b, which is fed into the column 1c via the feed line 2c at a charge rate of 494.00 kg/h, consists of 30 ppm of 4-chlorophthalic anhydride, 83% by weight of 3-chlorophthalic anhydride, 3.60% by weight of 4,5-dichlorophthalic anhydride, 6.90% by weight of 3,6-dichlorophthalic anhydride and 6.50% by weight of higher-boiling products. At a reflux ratio of 150, 29.80 kg per hour of a mixture which consists of 496 ppm of 4-chlorophthalic anhydride, 41.00% by weight of 3-chlorophthalic anhydride and 59.00% by weight of 4,5-dichlorophthalic anhydride are removed from the column 1c. In the bottom of the column 1c are found a further 0.10% by weight of 4,5-dichlorophthalic anhydride, 85.70% by weight of 3-chlorophthalic anhydride, 7.30% by weight of 3,6-dichlorophthalic anhydride and 6.90% by weight of higher-boiling products. The recovery of the 3-chlorophthalic anhydride, which only contains a further 0.1% by weight of 4,5-dichlorophthalic anhydride, takes place therefrom virtually quantitatively in the next column.

This example confirms that even at chlorination rates of phthalic anhydride which are of economic interest, very pure 3-chlorophthalic anhydride can be obtained.

EXAMPLE 2

A crude distillate such as in Example 1 was worked up in a similar manner, except that a residual content of 0.2% by weight of 4,5-dichlorophthalic anhydride in 3-chlorophthalic anhydride was to be obtained and for this reason a reflux ratio at the column top of the column 1c of 115 was selected. The mixture removed from the top of the column 1c in this Example at 29.20 kg/h consisted of 508 ppm of 4-chlorophthalic anhydride, 41% by weight of 3-chlorophthalic anhydride and 59% by weight of 4,5-dichlorophthalic anhydride. The bottom of the column 1c consisted of 85.60% by weight of 3-chlorophthalic anhydride, 0.20% by weight of 4,5-dichlorophthalic anhydride, 7.30% by weight of 3,6-dichlorophthalic anhydride and 6.90% by weight of higher-boiling products. 3-Chlorophthalic anhydride is then recovered virtually quantitatively from this with the residual content of 4,5-dichlorophthalic anhydride in the bottom given previously.

This example confirms that the purity of the 3-chlorophthalic, anhydride obtained can be controlled by the reflux ratio at the top of the column 1c.

EXAMPLE 3

From a crude distillate of a chlorination reaction of phthalic anhydride, consisting of 78.50% by weight of phthalic anhydride, 9.20% by weight of 4-chlorophthalic anhydride, 11.40% by weight of 3-chlorophthalic anhydride, 0.28% by weight of 4,5-dichlorophthalic anhydride, 0.41% by weight of 3,6-dichlorophthalic anhydride and 0.21% of higher-boiling products, 3-chlorophthalic anhydride having a residual content of 4,5-dichlorophthalic anhydride of 0.1% by weight is to be obtained. The crude distillate is fed into the column 1a at the height of the 15th step at a charge rate of 2000 kg/h. The distillate which is removed via the line 7a of the column 1a contains 99.50% by weight of phthalic anhydride and 0.50% by weight of 4-chlorophthalic anhydride at a reflux ratio of 17. From the column 1b via the line 7b, a distillate is removed at a reflux ratio of 312 which consists of 0.50% by weight of phthalic anhydride and 99.50% by weight of 4-chlorophthalic anhydride and also 10 ppm of 3-chlorophthalic anhydride. The bottom of the column 1b, which is fed into the column 1c at a charge rate of 246.00 kg/h via the feed line 2c, consists of 30 ppm of 4-chlorophthalic anhydride, 92.70% by weight of 3-chlorophthalic anhydride, 2.30% by weight of 4,5-dichlorophthalic anhydride, 3.30% by weight of 3,6-dichlorophthalic anhydride and 1.70% by weight of higher-boiling products. At a reflux ratio of 247, 9.20 kg per hour of a mixture which consists of 805 ppm of 4-chlorophthalic anhydride, 41.30% by weight of 3-chlorophthalic anhydride and 58.705 by weight of 4,5-dichlorophthalic anhydride are removed from the column 1c. In the bottom of the column 1c are found a further 0.10% by weight of 4,5-dichlorophthalic anhydride, 94.70% by weight of 3-chlorophthalic anhydride, 3.40% by weight of 3,6-dichlorophthalic anhydride and 1.80% by weight of higher-boiling products. The recovery of the 3-chlorophthalic anhydride, which only contains a further 0.1% by weight of 4,5-dichlorophthalic anhydride, takes place virtually quantitatively therefrom in a further column.

This example confirms that the intermediate fraction which contains both 3-chlorophthalic anhydride and 4,5-dichlorophthalic anhydride can be kept small if the crude distillate only contains small amounts of 4,5-dichlorophthalic an hydride, and that in this case a lower reflux ratio is adequate for additionally obtaining the same purity of 3-chlorophthalic anhydride.

EXAMPLE 4

A crude distillate as in Example 3 was worked up in the same manner as in this example, except that a residual content of 0.2% by weight of 4,5-dichlorophthalic anhydride in 3-chlorophthalic anhydride was to be obtained and for this reason a reflux ratio at the column top of the column 1c of 150 was selected. The mixture removed at the top of the column 1c in this Example at 8.80 kg/h consisted of 837 ppm of 4-chlorophthalic anhydride, 40.91% by weight of 3-chlorophthalic anhydride and 59.09% by weight of 4,5-dichlorophthalic anhydride. The bottom consisted of 94.60% by weight of 3-chlorophthalic anhydride, 0.20% by weight of 4,5-dichlorophthalic anhydride, 3.40% by weight of 3,6-dichlorophthalic anhydride and 1.80% by weight of higher-boiling products. 3-Chlorophthalic anhydride was recovered virtually quantitatively therefrom with a residual content of 0.20% by weight of 4,5-dichlorophthalic anhydride.

This example again confirms that the purity of the 3-chlorophthalic anhydride obtained can be controlled solely by the reflux ratio at the top of the column 1c.

We claim:

1. A process for preparing substantially pure 3-chlorophthalic anhydride from a starting chlorination products mixture which contains 4,5-dichlorophthalic anhydride in addition to 3-chlorophthalic anhydride, which comprises first distilling off a mixture of 3-chlorophthalic anhydride and 4,5-dichlorophthalic anhydride from the starting chlorination products mixture in a distillation step (a), so that the bottom obtained is essentially free of 4,5-dichlorophthalic anhydride, and then, by distillation of the bottom obtained, recovering 3-chlorophthalic anhydride from chlorination products in a distillation step (b), wherein the purity of the 3-chlorophthalic anhydride is controlled by reflux ratio during the separation of the mixture of 3-chlorophthalic anhydride and 4,5-dichlorophthalic anhydride in the distillation step (a).

2. A process as claimed in claim 1, wherein the mixture of 3-chlorophthalic anhydride and 4,5-dichlorophthalic anhydride is distilled off in the first distillation step (a) at from 2.5 to 80 kPa, and from 185° to 300° C.

3. A process as claimed in claim 1, wherein the starting mixture is prepared by incomplete chlorination of phthalic anhydride, from which unreacted phthalic anhydride has been removed by continuous or batchwise distillation.

4. A process as claimed in claim 3, wherein the starting mixture is prepared without solvent in a melt using $FeCl_3$ as a catalyst.

5. A process as claimed in claim 3, wherein the unreacted phthalic anhydride is fed back into the chlorination step for preparing the starting mixture.

6. A process as claimed in claim 1, wherein the mixture of 3-chlorophthalic anhydride and 4,5-dichlorophthalic anhydride obtained in the distillation step (a) is processed further to give perchlorophthalic anhydride.

7. A process as claimed in claim 1, wherein the chlorination products remaining in the bottom after the distillation step (b) are processed further to give perchlorophthalic anhydride.

8. A process for the production of substantially pure 3-chlorophthalic anhydride which comprises chlorinating phthalic anhydride with partial conversion to obtain a chlorination products mixture, distilling off unreacted phthalic anhydride as a top product, distilling off 4-chlorophthalic anhydride as a second top product, then distilling off a mixture of 4,5-dichlorophthalic anhydride and 3-dichlorophthalic anhydride as a third top product to obtain a bottoms product which is essentially free of 4,5-dichlorophthalic anhydride, and recovering by subsequent distillation substantially pure 3-dichlorophthalic anhydride.

9. A process as claimed in claim 8, wherein the purity of the 3-chlorophthalic anhydride is controlled by reflux ratio during the distillation of the mixture of 3-chlorophthalic anhydride and 4,5-dichlorophthalic anhydride.

10. A process as claimed in claim 8, wherein the mixture of 3-chlorophthalic anhydride and 4,5-dichlorophthalic anhydride is distilled off at from 2.5 to 80 kPa and from 185° to 300° C.

* * * * *